US00PP09007P

United States Patent [19]

Austin

[11] Patent Number: Plant 9,007

[45] Date of Patent: Dec. 13, 1994

[54] SHRUB ROSE PLANT NAMED AUSCOMP

[75] Inventor: David C. H. Austin, Albrighton, England

[73] Assignee: David Austin Roses Limited, Albrighton, England

[21] Appl. No.: 181,987

[22] Filed: Jan. 13, 1994

[51] Int. Cl.[5] ..... A01H 5/00

[52] U.S. Cl. ..... Plt./1

[58] Field of Search ..... Plt. 1, 24

U.S. PATENT DOCUMENTS

PLT 8678 4/1994 Austin ..... PLT/1
PLT 8682 4/1994 Austin ..... PLT/1
PLT 8688 4/1994 Austin ..... PLT/1

*Primary Examiner*—Howard J. Locker
*Attorney, Agent, or Firm*—Klarquist Sparkman Campbell Leigh & Whinston

[57] ABSTRACT

A shrub rose having full, double, bright yellow flowers; moderately strong, sweet fragrance; repeat flowering; and bushy growth.

1 Drawing Sheet

The present invention relates to a new and distinct variety of rose plant of the shrub class which was originated by me by crossing an unnamed seedling having semi-double, creamy white flowers resulting from a cross of the variety "Iceberg" with another unnamed seedling, with the variety AUShero.

The primary objective of this breeding was to produce a new shrub rose variety that is repeat-flowering and has old-fashioned-type flowers. The objective was substantially achieved, along with other desirable improvements, as evidenced by the following unique combination of characteristics that are outstanding in the new variety and that distinguish it from its parents, as well as from all other varieties of which I am aware:

1. Full, double flowers;
2. Bright yellow flowers;
3. Moderately strong, sweet fragrance;
4. Repeat flowering; and
5. Bushy growth.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in differenct stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling of "Iceberg" (unpatented).

*Pollen parent.*—AUShero (unpatented).

Classification:

*Botanical.*—*Rosa Hybrida.*

*Commercial.*—Shrub.

FLOWER

Observations made from specimens grown in a garden environment at Albrighton, Wolverhampton, England, in Jul. 1992.

Blooming habit: Recurrent.

Bud:

*Size.*—About 3 cm long when the petals start to unfurl.

*Form.*—The bud form is pointed ovoid, broad-based.

*Color.*—When sepals first divide, bud color is Yellow-Green Group 145B/C. When half blown, the upper sides of the petals are Yellow Group 12A; and the lower sides of the petals are Yellow Group 12B.

*Sepals.*—Color: Yellow-Green Group 144A/B. Surface texture: Leathery, slightly puckered. There are three normally appendaged sepals. There are two unappendaged sepals with smooth or somewhat downy edges.

*Receptacle.*—Color: Yellow-Green 144A/B. Shape: Funnel shaped. Size: Large, broad (about 12 mm×15 mm). Surface: Smooth.

*Peduncle.*—Length: Averaging about 3 to 4 cm. Surface: Smooth. Color: Light green, bronzy blush. Strength: Somewhat bending.

Bloom:

*Size.*—Average open diameter is 9.5 cm.

*Borne.*—In irregularly shaped clusters of 4 to 7 flowers per stem.

*Stems.*—Average length is about 60 to 70 cm; normal strength.

*Form.*—When first open: Bloom is cupped. Permanence: Flattens. Inner petals and petaloids tucked into calyx; outer petals curl back.

*Petalage.*—Mean number of petals under normal conditions: 150 to 160.

*Color.*—The upper side of the petals is Yellow Group 12B. The reverse side of the petals is Yellow Group 12C. The base of each petal has a Yellow Group 13A tip. The major color on the upper side is Yellow Group 12B.

*Variegations.*—None.

*Discoloration.*—The general tonality at the end of the first day: Slightly paler than at the beginning of the day. At the end of the third day, paler but more lemon, less gold, tending to Yellow Group 6D.

*Fragrance.*—Moderately strong, sweet tea-rose fragrance.

Petals:

*Texture.*—Medium.

*Shape.*—Outer petals cupped, round, notched; inner petals more deltoid; edges of petals pucker when aging.

*Form.*—Edges slightly quilled; inner petals and petaloids tucked into calyx to form a button.

*Arrangement.*—Informal, with many large petaloids in the center.

*Persistence.*—Petals tend to drop off cleanly before drying.

*Lastingness.*—On the plant: About 3 to 4 days. As a cut flower: About 3 to 4 days.

Reproductive parts:

*Anthers.*—Size: Medium. Quantity: Few. Color: Yellow. Arrangement: Tucked into calyx or partly so; mixed with petaloids.

*Filaments.*—Color: Yellow.

*Pollen.*—Color: Gold yellow.

*Styles.*—Color: Base: white; top: deep pink.

*Stigmas.*—Color: Yellow.

Form: Shrub.

Growth: Vigorous. Mature plants have a height of slightly over 1 m. and width of about 75 cm.

Foliage: Number of leaflets on normal mid-stem leaves: 5.

*Size.*—Medium (about 16.5 cm long × 14 cm wide).

*Quantity.*—Normal number and distribution of leaves on stems for this class.

*Color.*—New foliage: Yellow-Green Group 146A. Old foliage: Yellow-Green Group 147A.

Leaflets:

*Shape.*—Elliptic.

*Texture.*—Upper side: Leathery, semi-glossy.

*Edge.*—Serrated.

*Serration.*—Single.

*Petiole rachis.*—Color: Green, reddish blush.

*Petiole underside.*—Mostly smooth; one or two prickles per petiole.

*Stipules.*—Serrated; about 2.5 to 3 cm long.

*Disease resistance.*—Resistant to mildew and blackspot under normal growing conditions at Albrighton, Wolverhampton, England.

Wood:

*New wood.*—Color: Light green. Bark: Smooth.

*Old wood.*—Color: Green. Bark: Smooth.

Prickles:

*Quantity.*—On main canes from base: Few. On laterals from main canes: Very few or none.

*Form.*—Medium to long; straight or slightly hooked downward.

*Color when young.*—Red.

*Position.*—Randomly distributed, mainly on lower nodes on main stems.

Small prickles:

*Quantity.*—On main stalks: None. On laterals: None.

I claim:

1. A new and distinct variety of rose plant of the shrub class, substantially as herein shown and described, characterized particularly as to novelty by the unique combination of its full, double, bright yellow flowers; moderately strong, sweet fragrance; repeat flowering; and bushy growth.

* * * * *

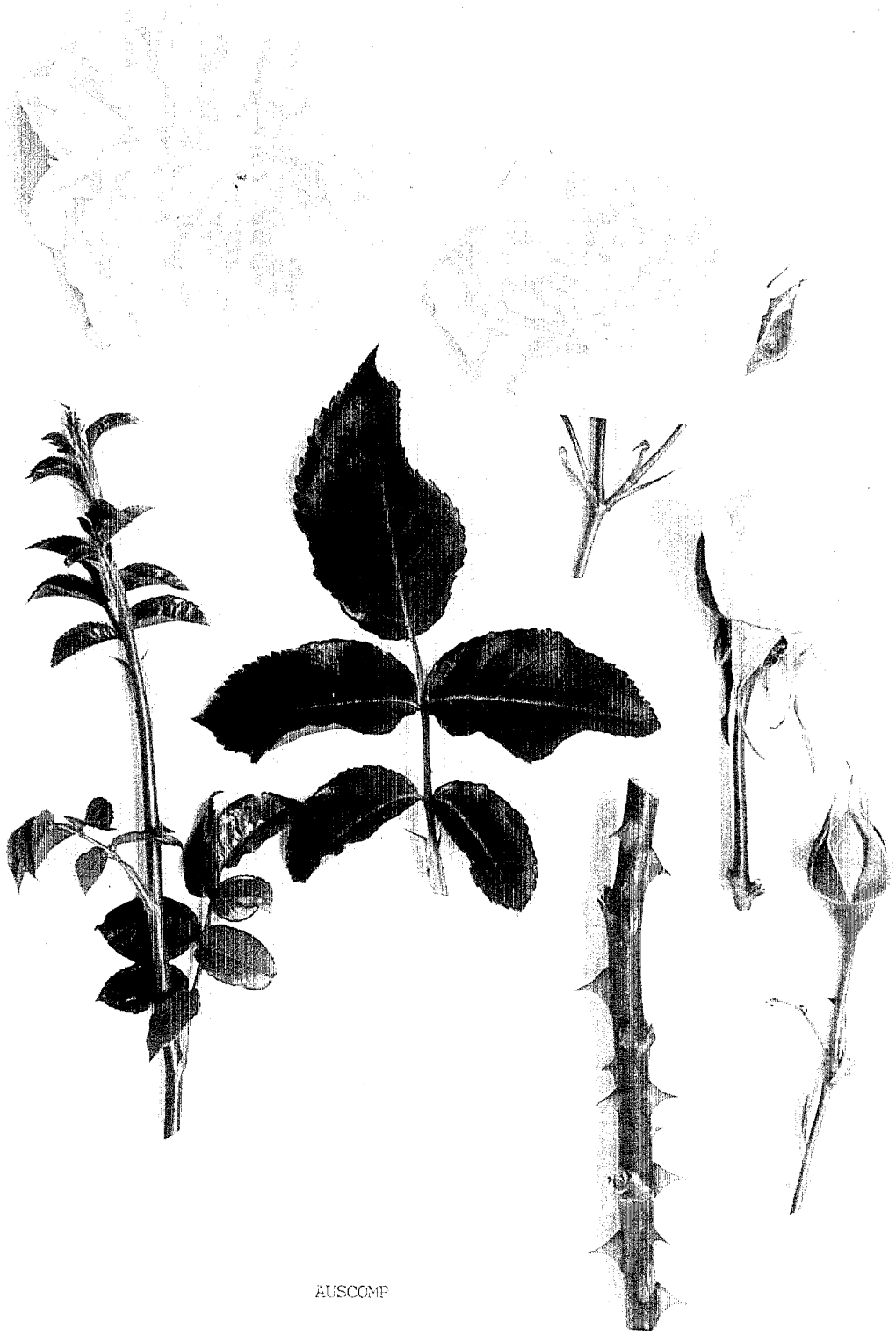
AUSCOMP